US009541550B2

(12) United States Patent
Takubo et al.

(10) Patent No.: US 9,541,550 B2
(45) Date of Patent: Jan. 10, 2017

(54) METHOD FOR IMMUNOLOGICALLY MEASURING SOLUBLE LR11

(75) Inventors: Kohei Takubo, Ryugasaki (JP); Hiroyuki Ebinuma, Ryugasaki (JP); Isamu Fukamachi, Ryugasaki (JP); Hideaki Bujo, Chiba (JP); Yasushi Saito, Chiba (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 348 days.

(21) Appl. No.: 14/116,683

(22) PCT Filed: May 9, 2012

(86) PCT No.: PCT/JP2012/061902
§ 371 (c)(1),
(2), (4) Date: Nov. 8, 2013

(87) PCT Pub. No.: WO2012/153773
PCT Pub. Date: Nov. 15, 2012

(65) Prior Publication Data
US 2014/0080158 A1   Mar. 20, 2014

(30) Foreign Application Priority Data
May 9, 2011   (JP) ................................. 2011-104423

(51) Int. Cl.
G01N 33/543   (2006.01)
G01N 33/92   (2006.01)

(52) U.S. Cl.
CPC ........ *G01N 33/54393* (2013.01); *G01N 33/92* (2013.01)

(58) Field of Classification Search
None
See application file for complete search history.

(56) References Cited

U.S. PATENT DOCUMENTS

| 5,665,872 A | 9/1997 | Saito et al. |
| 9,261,443 B2* | 2/2016 | Matsuo ................. C07K 16/28 |
| 2009/0269791 A1 | 10/2009 | Hill et al. |
| 2011/0091993 A1 | 4/2011 | Matsuo et al. |
| 2011/0104714 A1 | 5/2011 | Hill et al. |
| 2011/0177610 A1 | 7/2011 | Matsuo et al. |
| 2011/0182940 A1 | 7/2011 | Takahashi et al. |
| 2013/0029363 A1 | 1/2013 | Ebinuma et al. |
| 2013/0115229 A1 | 5/2013 | Ebinuma et al. |

FOREIGN PATENT DOCUMENTS

| CN | 1751128 A | 3/2006 |
| CN | 101975850 A | 2/2011 |
| EP | 2 159 577 A1 | 3/2010 |
| EP | 2 256 497 A1 | 12/2010 |
| JP | 9 163988 | 6/1997 |
| JP | 2010 104365 | 5/2010 |
| WO | WO 2004/059293 A2 | 7/2004 |
| WO | WO 2004/059293 A3 | 7/2004 |
| WO | 2008 155891 | 12/2008 |
| WO | 2009 116268 | 9/2009 |
| WO | 2009 134852 | 11/2009 |
| WO | WO 2010/038719 A1 | 4/2010 |

OTHER PUBLICATIONS

Churchward et al., "Enhanced detergent extraction for analysis of membrane proteomes by two-dimensional gel electrophoresis," Proteome Sci., 2005, vol. 7, No. 3, pp. 1-11.*
Office Action and Search Report issued on Aug. 28, 2014 in the corresponding Chinese patent Application No. 201280022119.8 (with partial English translation).
Masanao Matsuo, et al., "Development of an Immunoassay for the Quantification of Soluble LR11, a Circulating Marker of Atherosclerosis", Clinical Chemistry, Proteomics and Protein Markers, vol. 55, No. 10, Aug. 6, 2009, pp. 1801-1808.
Zheng Yan-cheng, et al., "The Synthesis and Properties of Sulphobetaine Surfactants", Journal of Yangtze University (Natural Science Edition), vol. 7, No. 3, Sep. 15, 2010, 5 pages.
Yamazaki, H. et al., "Elements of Neural Adhesion Molecules and a Yeast Vacuolar Protein Sorting Receptor Are Present in a Novel Mammalian Low Density Lipoprotein Receptor Family Member", The Journal of Biological Chemistry, vol. 271, No. 40, pp. 24761-24768, (1996).
Kanaki, T. et al., "Expression of LR11, a Mosaic LDL Receptor Family Member, Is Markedly Increased in Atherosclerotic Lesions", Arteriosclerosis, Thrombosis, and Vascular Biology, Journal of the American Heart Association, vol. 19, pp. 2687-2695, (1999).
Zhu, Y. et al., "LR11, an LDL Receptor Gene Family Member, Is a Novel Regulator of Smooth Muscle Cell Migration" Circulation Research, vol. 94, pp. 752-758, (Apr. 2, 2004).
Bujo, Hideaki, "Physiologically active substance capable of acting on lesion of arteriosclerosis or lesion formation process and condition of disorder", A Novel Biomarker of Intimal Smooth Muscle Cells: LR11, Igaku No Ayumi, vol. 221, No. 13, pp. 1200-1203, (Jun. 30, 2007) (with partial English translation).
Jiang, M. et al., "Ang ||-Stimulated migration of vascular smooth muscle cells is dependent on LR11 in mice", The Journal of Clinical Investigation, vol. 118, No. 8, pp. 2733-2746, (Aug. 2008).
Masaki, T. et al., The 39th Annual Scientific Meeting of the Japan Atherosclerosis Society—Abstract, General lecture subject (poster) 189, p. 264, Total (3 Pages) (with English translation).

(Continued)

*Primary Examiner* — Galina Yakovleva
(74) *Attorney, Agent, or Firm* — Oblon, McClelland, Maier & Neustadt, L.L.P.

(57) ABSTRACT

To provide a method for assaying soluble LR11 in a biological sample, which method realizes a simple and accurate assay of soluble LR11 present in the sample by immunological means without requiring isolation of soluble LR11 from the biological sample (e.g., a serum sample).
The method of the invention for immunologically assaying soluble LR11 present in a biological sample, characterized in that the method includes treating the sample with at least one surfactant selected from among one or more sulfobetaine amphoteric surfactants and one or more amidosulfobetaine amphoteric surfactants.

3 Claims, 5 Drawing Sheets

(56) References Cited

OTHER PUBLICATIONS

International Search Report Issued Jun. 5, 2012 in PCT/JP12/061902 Filed May 9, 2012.
Extended European Search Report issued Nov. 18, 2014 in Patent Application No. 12782440.7.
Wolfgang Hampe, et al., "Ectodomain shedding, translocation and synthesis of SorLA are stimulated by its ligand head activator" Journal of Cell Science, vol. 113, No. 24, XP009164186, 2000, pp. 4475-4485.

* cited by examiner

US 9,541,550 B2

METHOD FOR IMMUNOLOGICALLY MEASURING SOLUBLE LR11

TECHNICAL FIELD

The present invention relates to a method for immunologically assaying soluble LR11 present in a biological sample.

BACKGROUND ART

LDL receptor relative with 11 ligand-binding repeats (LR11) is an LDL receptor-like protein having a structure characteristic to the LDL receptor family and a molecular weight of about 250 kD (Patent Document 1, Non-Patent Document 1). In addition to membrane-bound type LR11, soluble LR11, a segment cleaved by protease is known as LR11 (Non-Patent Document 4). It is reported that little or no expression of LR11 was observed in normal vascular wall cells, but expression thereof was observed specifically in thickened intima smooth muscle cells (Non-Patent Document 2). Moreover, it is reported that expression of LR11 was promoted in response to proliferation of cultured smooth muscle cells, leading to secretion of soluble LR11 to the culture liquid, and that thickening of vascular intima, which would be caused by migration and proliferation of smooth muscle cells, is inhibited in a cuff injury mouse model by functionally impairing LR11 gene in the mouse by developmental engineering (Non-Patent Document 3). Furthermore, the present inventors previously found that the blood soluble LR11 levels of arteriosclerosis patients are significantly higher than those of healthy subjects, and reported that the blood soluble LR11 could be used as a new marker for arteriosclerosis (Non-Patent Document 5, Patent Document 2).

Hitherto, there is a known method for determining soluble LR11 through separating soluble LR11 from a sample by use of an insoluble carrier to which a chaperone molecule, a receptor associated protein (RAP) having affinity to LR11, has been bound, followed by performing SDS-PAGE and Western blotting to detect LR11 through immunostaining by use of an anti-LR11 antibody (Non-Patent Documents 5, 6). However, since the known method includes cumbersome steps such as separation of soluble LR11 from a sample, the method is not practical for application to clinical tests or the like.

The present inventors previously tried to establish an immunological assay method employing an anti-soluble LR11 antibody, as a simple and practical soluble LR11 determination method. However, when a biological sample such as a serum sample was analyzed, an unidentified interfering substance present in the biological sample (hereinafter may be referred to simply as an "interfering substance") was found to interfere with correct determination of soluble LR11.

Therefore, the present inventors extensively studied on means for eliminating the effects of interfering substances on the immunological assay method. As a result, the inventors found that, when a biological sample such as a serum sample is mixed with a specific surfactant such as N-acyl-N-methylglucamine, and the thus-treated sample is subjected to an immunological assay, soluble LR11 present in the sample can be correctly determined in a simple manner while eliminating the effects of interfering substances, and the inventors previously filed a patent application (Patent Document 3).

PRIOR ART DOCUMENTS

Patent Documents

Patent Document 1: JP-A-H9 (1997)-163988
Patent Document 2: WO2008/155891
Patent Document 3: WO2009/116268

Non-Patent Documents

Non-Patent Document 1: J. Biol. Chem. 1996; 271, p. 24761-24768
Non-Patent Document 2: Arterioscler. Thromb. Vasc. Biol. 1999; 19, p. 2687-2695
Non-Patent Document 3: Circ. Res. 2004; 94, p. 752-758
Non-Patent Document 4: Journal of Clinical and Experimental Medicine, Vol. 221, No. 13, p. 1200-1203
Non-Patent Document 5: J. Clin. Invest. 2008; 118, p. 2733-2746
Non-Patent Document 6: Program and Abstracts, The 39th Annual Scientific Meeting of the Japan Arteriosclerosis Society, General Lecture (poster) 189, p. 264

SUMMARY OF THE INVENTION

Problems to be Solved by the Invention

However, the conventional method disclosed in Patent Document 3 (hereinafter may be referred to simply as the "conventional method"), for example, a method for assaying a human serum sample treated with N-acyl-N-methylglucamine by sandwich ELISA employing two anti-soluble LR11 antibodies requires one night at room temperature for completing reaction between immobilized anti-soluble LR11 antibodies and soluble LR11 (hereinafter may be referred to as "primary reaction"). Therefore, the conventional method has a problem of requiring two days for the assay. Then, the inventors of the present application tried to shorten the time of primary reaction performed in the conventional method, and found that absorbance values of the analyzed samples lowered due to shortening of the primary reaction time, and also found that the degree of the drop in absorbance due to shortening of the primary reaction time in some samples differs from that in the other samples, and thus the correlation between the samples in the measurements (of soluble LR11 level) obtained by the conventional method differs from that obtained by the aforementioned method in which the primary reaction time was shortened. In other words, the inventors revealed that the correlation in measurements between the conventional method and the aforementioned method in which the primary reaction time was shortened may be lowered in some case.

Therefore, an object of the present invention is to provide a more practical method for immunologically assaying soluble LR11 in a biological sample, which method can shorten the assay time without affecting the correlation between the samples obtained through the conventional method.

Means for Solving the Problems

The present inventors have carried out extensive studies in order to attain the aforementioned object, and have found that, soluble LR11 level-dependent measurement results can be obtained without affecting the correlation between the samples obtained through the conventional method when a sample which has been treated with a sulfobetaine amphoteric surfactant or an amidosulfobetaine amphoteric surfactant is subjected to an immunological assay, even though the effects of interfering substances present in a sample is eliminated similarly to the case of N-acyl-N-methylglucamine or the like disclosed in Patent Document 3 and the primary reaction time is shortened for example to one hour at room temperature. The present invention has been accomplished on the basis of this finding.

In other words, the present invention provides a method for immunologically assaying soluble LR11 present in a biological-sample, characterized in that the method comprises treating the sample with one or more surfactants selected from one or more sulfobetaine amphoteric surfactants and one or more amidosulfobetaine amphoteric surfactants.

The present invention also provides a reagent for soluble LR11 immunological assay, characterized in that the reagent comprises an anti-soluble LR11 antibody, and at least one surfactant selected from one or more sulfobetaine amphoteric surfactants and one or more amidosulfobetaine amphoteric surfactants.

Effects of the Invention

According to the immunological assay method and the immunological assay reagent of the present invention, soluble LR11 concentration present in a biological sample such as a blood sample can be quantitated within a shorter period of time still in a simple manner at high sensitivity even after considerably shortening the time of reaction between an anti-soluble LR11 antibody and soluble LR11 (e.g., reaction between an immobilized anti-soluble LR11 antibody and soluble LR11) for example from one night as disclosed in Patent Document 3 to one hour.

MODES FOR CARRYING OUT THE INVENTION

Figure 1:
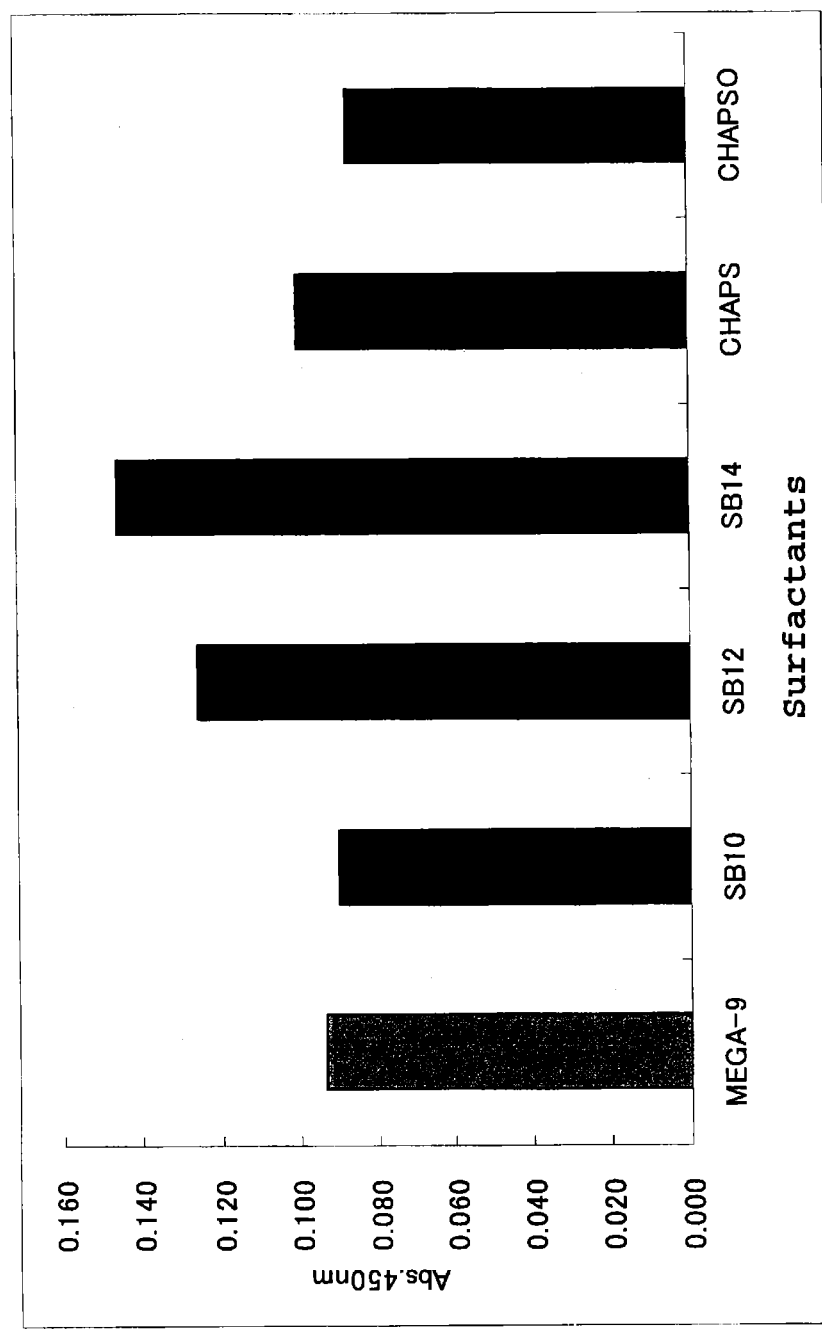
FIG. 1 A graph showing the soluble LR11 measurements obtained when primary reaction was performed for 16 hours and a surfactant disclosed in Patent Document 3 or the amphoteric surfactant of the present invention was employed.

The assay method of the present invention is directed to a method for immunologically assaying soluble LR11 present in a biological sample. Examples of the organism from which the biological sample is collected include mammals including human, such as human, monkey, horse, cow, pig, rabbit, rat, guinea pig, and mouse. Examples of the biological sample include body fluid samples such as blood, plasma, serum, cerebrospinal fluid, and urine; tissue samples such as blood vessel, organ, and muscle; cell samples such as cells isolated from organs, and leucocytes; and solution samples including ingredients derived from the above described materials (e.g., diluted sample liquid, homogenate, solution, and extract).

No particular limitation is imposed on the type of the immunological assay method of the present invention, so long as the method is a soluble LR11 assay on the basis of antigen-antibody reaction. However, the assay method preferably includes a step for the formation of an immune complex with at least two antibodies having different antigen-recognition sites. Examples of the assay method including a step for the formation of an immune complex with at least two antibodies having different antigen-recognition sites include the below-described assay methods, for example, sandwich ELISA, immunoturbidimetry (TIA or LTIA (latex turbidimetric immunoassay)), and immunochromatography.

The anti-soluble LR11 antibody may be a monoclonal antibody or a polyclonal antibody, so long as the antibody reacts with soluble LR11 present in the biological sample, for example, soluble LR11 purified from a mammal serum. Of these, a monoclonal antibody is preferably used. The antibody may be produced through a widely known method. As used herein, the term "anti-soluble LR11 antibody" refers to any antibody as long as it may react with soluble LR 11 present in the biological sample, as described above. Specifically, an antibody that reacts with membrane-bound LR11 present on cell surfaces, and an antibody disclosed in documents simply as "anti-LR11 antibody" may also be used in the present invention.

Examples of the animal which may be immunized for producing a polyclonal antibody include mouse, rat, hamster, rabbit, goat, sheep, and chicken. The anti-soluble LR11 anti-serum may be obtained by administering an antigen to an animal one or a plurality of times subcutaneously, intradermally, intraperitoneally, or in a similar manner, and recovering from the collected blood from the animal. Upon immunization, the antigen is preferably administered as a mixture with an adjuvant having immuno-potentiation effect.

The monoclonal antibody may be produced through a known method for producing a monoclonal antibody; e.g., "Monoclonal Antibody" (Hideaki NAGAMUNE and Hiroshi TERADA, Hirokawa-shoten, 1990) or "Monoclonal Antibody" (Jame W. Golding, 3rd edition, Academic Press, 1996). Also, the monoclonal antibody may be produced through DNA immunization technique (see, for example, Nature 1992 March 12; 356 pp. 152-154 or J. Immunol. Methods March 1; 249 pp. 147-154).

The antigen employed in production of the antibody may be LR11 protein or a fragment thereof (peptide). The LR11 protein may be obtained from blood, urine, and culture supernatant of the cells that extracellularly secrete soluble LR11 (e.g., smooth muscle cells and hematopoietic organ tumor cells), with an optional process such as purification. Alternatively, hematopoietic organ tumor cells having LR11 produced on the cell surfaces may be used per se as an antigen (WO2012/008595). The aforementioned peptide may be produced by digesting the aforementioned protein with a protease and subjecting the product to a treatment such as purification. Alternatively, synthetic peptide may also be used. Examples of the peptide include a peptide having an amino acid sequence disclosed in Patent Document 3. The amino acid sequence of the peptide may have one or several deletion, substitution, or addition of amino acid.

For producing the antibody through DNA immunization, LR11 protein or a vector into which cDNA encoding a fragment of the protein (the peptide) has been incorporated is administered into an animal to be immunized, and the antigen is generated in the animal to thereby immunize the animal. Examples of the peptide include a peptide having an amino acid sequence disclosed in Patent Document 3. The amino acid sequence of the peptide may have one or several deletion, substitution, or addition of amino acid.

In order to produce a monoclonal antibody which recognizes the high-order structure of LR11, a full-length LR11 vector, which is a construct including a full-length human LR11 gene, is the most suitably used. Alternatively, a vector into which a gene encoding a fragment of the LR11 protein (the peptide) has been incorporated may be also used.

In one mode of DNA immunization, the aforementioned vector (single component) or vectors (mixture) are subcutaneously injected to an animal (mouse, rat, etc.) via any of various known transfection methods (e.g., intramuscular injection, electroporation, and gene gun-mediated immunization) for incorporation of the vector(s) into animal-derived cells.

The monoclonal antibody production method employing the peptide antigen, or the monoclonal antibody production method through DNA immunization may be based on the method disclosed in Patent Document 3, and such reference is preferred. Examples of the anti-soluble LR11 monoclonal antibody include A2-2-3 antibody (produced by immunizing a mouse with the synthetic peptide disclosed in Patent Document 3), mouse monoclonal antibodies M3 and M5 (obtained through DNA immunization), and rat monoclonal antibodies R14 and R23 (obtained through DNA immunization).

In the assay method of the present invention, a sample which has been treated with at least one species of a sulfobetaine amphoteric surfactant and an amidosulfobetaine amphoteric surfactant is subjected to an immunological assay. Through the aforementioned treatment, the effects of LR11 assay interfering substances present in the sample can be eliminated. Also, even when the primary reaction time is shortened for example, to one hour at room temperature, soluble LR11 level-dependent measurement results can be obtained, without affecting the concentration-absorbance relationship obtained through the conventional method.

The sulfobetaine amphoteric surfactant or the amidosulfobetaine amphoteric surfactant employed in the present invention is preferably a compound represented by the following formula (1) or (2):

[F1]

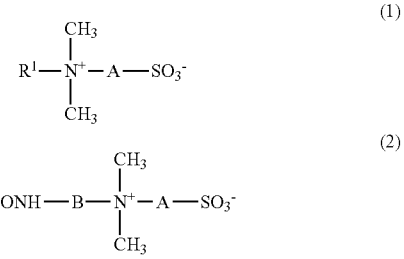

(wherein $R^1$ represents a C6 to C18 alkyl group or alkenyl group; $R^2CO$ represents a C6 to C18 acyl group or cholic acid-derived acyl group; A represents a C2 to C5 alkylene group or a C2 to C5 hydroxyalkylene group; and B represents a C1 to C5 alkylene group).

Examples of the C6 to C18 alkyl group or alkenyl group of $R^1$ include linear-chain and branched alkyl groups and alkenyl groups. Among them, linear-chain and branched alkyl groups are preferred, with linear-chain alkyl groups being more preferred. The alkyl group or alkenyl group preferably contains 6 to 14 carbon atoms, more preferably 8 to 14 carbon atoms, particularly preferably 10 to 14 carbon atoms. Among the alkyl groups and alkenyl groups represented by $R^1$, decyl, dodecyl, tetradecyl are particularly preferred.

Examples of the C6 to C18 acyl group of $R^2CO$ include C6 to C18 aliphatic acyl groups. Specific examples include hexanoyl, octanoyl, decanoyl, dodecanoyl, tetradecanoyl, hexadecanoyl, and octadecanoyl. $R^2CO$ is preferably an acyl group derived from cholic acid.

Examples of the C2 to C5 alkylene group of A include ethylene, trimethylene, tetramethylene, and pentamethylene. Among them, ethylene and trimethylene are more preferred. Examples of the C2 to C5 hydroxyalkylene group of A include a hydroxytrimethylene group represented by —$CH_2CH(OH)CH_2$—.

Examples of the C1 to C5 alkylene group of B include methylene, ethylene, trimethylene, tetramethylene, and pentamethylene.

Examples of the commercially available product of the sulfobetaine amphoteric surfactant represented by formula (1) include Sulfobetaine 10 (SB10: $R^1=C_{10}H_{23}$, A=—($CH_2)_3$—), Sulfobetaine 12 (SB12: $R^1=C_{12}H_{25}$, A=—($CH_2)_3$—), and Sulfobetaine 14 (SB14: $R^1=C_{14}H_{29}$, A=—($CH_2)_3$—) (products of AMRESCO), which are suitably used in the present invention. Examples of the commercially available product of the amidosulfobetaine amphoteric surfactant represented by formula (2) include 3-[(3-cholamidopropyl)dimethylammonio]propanesulfonate (CHAPS: $R^2CO$=cholic acid-derived acyl, A=—($CH_2)_3$—), B=—($CH_2)_3$—), and 3-[(3-cholamidopropyl)dimethylammonio]-2-hydroxypropanesulfonate (CHAPSO: $R^2CO$=cholic acid-derived acyl, A=-$CH_2CH(OH)CH_2$—, B=—($CH_2)_3$—) (products of Dojindo), which are suitably used in the present invention.

In the treatment of the biological sample with at least one surfactant selected from among one or more sulfobetaine amphoteric surfactants and one or more amidosulfobetaine amphoteric surfactants, the specific amphoteric surfactant shall be present in the biological sample before or during the immunoassay. Preferably, the sample is mixed with the surfactant before the immunoassay. In one method of mixing the sample with the surfactant, the amphoteric surfactant of the present invention is incorporated into a sample-diluting liquid, and the sample is diluted with the liquid. In another method, the amphoteric surfactant of the present invention is incorporated into a reagent containing an anti-soluble LR11 antibody in advance, and soluble LR11 present in the sample is reacted with the anti-soluble LR11 antibody. A specific embodiment of the method is sandwich ELISA employing a microplate, in which a non-diluted or preliminarily diluted sample is added to the wells filled with an enzyme-labeled anti-soluble LR11 antibody solution. In still another method, the surfactant is incorporated into a member for receiving a sample in advance (e.g., a sample pad employed in immunochromatography), and the sample is made to pass through the member.

As used herein, the term "sample-diluting liquid" refers to a liquid for directly or indirectly adjusting (diluting) the soluble LR11 concentration of the biological sample to a level suited for immune reaction. The sample-diluting liquid may be called any name such as "preliminary treatment liquid" or "first reagent (liquid)."

The amphoteric surfactant concentration employed in the present invention may be appropriately determined in consideration of the feature of the employed assay method, the type of the employed amphoteric surfactant, the ratio of soluble LR11 concentration to amphoteric surfactant concentration in the sample containing the amphoteric surfactant of the present invention, and other factors. For example, when the sample containing soluble LR11 is co-present with the surfactant, the surfactant concentration is preferably 0.001 to 10 mass %, more preferably 0.001 to 5 mass %, yet more preferably 0.05 to 5 mass %. In sandwich ELISA, the surfactant concentration is preferably 0.1 to 5 mass %, more preferably 0.5 to 5 mass %. In sandwich LTIA, the surfactant concentration is preferably 0.001 to 3 mass %, more preferably 0.05 to 2 mass %. Needless to say, those skilled in the art can modify, based on the above indices, the concentration to fall outside the aforementioned ranges. The biological sample is preferably treated with the amphoteric surfactant of the present invention at 5 to 40° C., particularly preferably at 10 to 30° C. The period of time of the treatment of the biological sample with the amphoteric surfactant of the present invention may be appropriately determined according to the type and concentration of the employed amphoteric surfactant, temperature, and other conditions. When the biological sample is treated with the amphoteric surfactant of the present invention, the time of reaction between soluble LR11 present in the biological sample and the anti-soluble LR11 antibody can be shortened as compared with that required in a conventional method (e.g., a method disclosed in Patent Document 3 employing N-acyl-N-methylglucamine). According to the method of the present invention, the time required for assaying soluble LR11 in a biological sample can be remarkably shortened.

In accordance with the design of the assay system (e.g., detection sensitivity or reaction time), the biological sample may be diluted to a factor of 1 (non-diluted) to 50. The dilution process may be performed by use of the sample-dilution liquid containing the amphoteric surfactant of the present invention, or a buffer or the like not containing the amphoteric surfactant of the present invention. However, use of the sample-dilution liquid containing the amphoteric surfactant of the present invention makes the assay operation easier. In the assay, the biological sample is preferably diluted with the sample-dilution liquid at a dilution factor of 4 to 30. No particular limitation is imposed on the composition of the sample-dilution liquid, so long as the effects of the present invention are not impaired, and the composition can be employed in a typical immunological assay method. Examples of ingredients of the sample-dilution liquid which can be employed in the present invention include buffers such as GOOD buffer, phosphate buffer, glycine buffer, carbonate buffer, and Tris buffer (pH: falling within a range employed in a typical immunological assay method), salts such as NaCl; protein components such as BSA; surfactants other than the amphoteric surfactant of the present invention; and commercially available non-specific reaction inhibitors.

So long as a sample containing the aforementioned specific amphoteric surfactant is used, immunological assay employing an anti-soluble LR11 antibody is performed through a typical conventional method.

As described above, no particular limitation is imposed on the immunological assay method, so long as the assay is a soluble LR11 assay employing antigen-antibody reaction. However, the assay method preferably includes a step for the formation of an immune complex with at least two antibodies having different antigen-recognition sites. Examples of the assay method including a step for the formation of an immune complex with at least two antibodies having different antigen-recognition sites include sandwich ELISA (enzyme-linked immunosorbent assay), immunoturbidimetry (TIA or LTIA), and immunochromatography. As is clear from the aforementioned various embodiments, the immunological assay method of the present invention may be of a heterogeneous type or a homogeneous type. Briefly, the assay system is designed so that the sample treated with the amphoteric surfactant of the present invention undergoes antigen-antibody reaction one or more times with an anti-soluble LR11 antibody.

In the present specification, in some cases, antigen-antibody reaction is described distinctively as "primary reaction" or "secondary reaction," which is provided for describing the type of the embodiment (e.g., inclusion of a plurality of reaction steps). Such descriptions should not be construed as limiting the invention thereto.

No particular limitation is imposed on the detection means employed in the aforementioned assay methods. In sandwich ELISA, an enzyme immunoassay employing a chromogenic substrate/chromogenic agent, a luminescent substrate/a luminescent agent, a fluorescent substrate/fluorescent agent, etc.; a luminescence (chemiluminescence, bioluminescence) immunoassay, or a fluorescence immunoassay, or the like can be employed. In immunoturbidimetry, a method in which turbidity attributed to formation of an immune complex is measured as absorbance or by scattered light can be employed. In immunochromatography, a method in which optical detection is performed by use of metal colloid particles or colored latex particles can be employed. Those skilled in the art can readily understand that the present invention is applicable to immunostaining (Western blotting), a competitive immunoassay, etc., so long as a sample treated with the aforementioned specific amphoteric surfactant is used, and immunological assay employing an anti-soluble LR11 antibody is performed through a typical conventional method.

In the case where soluble LR11 which reacts with an anti-soluble LR11 antibody is quantitatively or semi-quantitatively assayed, the measurement results are preferably compared with an LR11 standard. Examples of LR11 standards preferably employed in the present invention include a serum having a known soluble LR11 concentration, soluble LR11 recovered from cultured cells or a culture supernatant of smooth muscle cells or neuroblasts, urine-derived soluble LR11 (WO2012/008595), recombinant LR11, and the aforementioned synthetic peptide used as an immunogen in antibody production.

As described above, the term "quantitation, quantitative determination, or equivalents thereof" used in the present invention encompasses both "quantitative" meaning and "semi-quantitative" meaning. Furthermore, in the case where detection sensitivity is predetermined to provide a criterion for clinical disease diagnosis or in similar cases, the term also encompasses "detection" for detecting the presence or absence of soluble LR11.

Taking sandwich ELISA as an example, the aforementioned immunological assay will be described in detail. In one embodiment, an anti-soluble LR11 monoclonal antibody is immobilized onto an insoluble carrier in an appropriate buffer, to thereby prepare an immobilized antibody. A second anti-soluble LR11 monoclonal antibody that has an antigen-recognition site different from that of the first anti-soluble LR11 monoclonal antibody immobilized onto an insoluble carrier is labeled with an enzyme. A sample is reacted with the antibodies, and the enzymatic activity of the labeled second antibody is determined, whereby the soluble LR11 level of the sample can be determined. In an alternative embodiment, a biotin-labeled anti-soluble LR11 monoclonal antibody is used as a second antibody. After completion of reaction of the antibody with a sample, enzyme-labeled avidin is further reacted, and the activity of the labeled enzyme is determined, whereby the LR11 level of the sample can also be determined.

Examples of preferred insoluble carriers employed in the invention include synthetic polymers such as polystyrene, polyethylene, and polypropylene; glass; silicon; and insoluble polysaccharides (cross-linked dextran, polysaccharide). These carriers may be used in the form of sphere, rod, or microparticle, or as a test tube, a microplate, etc. In the case where the carrier is in the form of sphere, rod, test tube, or microplate, the antibody concentration shall be 1 to 10 µg/mL in production of an immobilized antibody. In the case of a microparticle carrier, the antibody concentration is 1 to 10 mg/mL. The buffer employed in production of an immobilized antibody is preferably a neutral to an alkaline buffer having a pH of 7 to 10; such as phosphate buffer, glycine buffer, carbonate buffer, or Tris buffer. Immobilization is preferably performed at 4° C. to 25° C. for 1 hour to 72 hours.

The enzyme-labeled antibody employed in the invention may be produced through a known method; such as a method of Nakane P. K. et al. (J. Histochem. Cytochem., 22, p. 1084-1089, 1974) or a method of Ishikawa et al. (Maleimide method: "Enzyme Immunoassay," 3rd edition, published by Igaku-Shoin Ltd.). Specifically, a non-fragmented immunoglobulin molecule or a fragment $F(ab')_2$ or $Fab'$, produced through limited digestion of a corresponding antibody with an appropriate protease, is labeled with an enzyme, to thereby prepare an enzyme-labeled antibody. Examples of the labeling enzyme include peroxidase, alkaline phosphatase, β-D-galactosidase, and glucose oxidase.

Although a biotin-labeled antibody may also be produced through a known method, a commercially available biotinylating reagent (e.g., Sulfo-NHS-Biotinylation Kit, product of PIERCE) may be used, to thereby facilitate the production of a biotin-labeled antibody.

Similarly, an enzyme-labeled avidin may also be produced through a known method. Alternatively, a commercially available product (e.g., StreptAvidin, Horseradish Peroxidase Conjugated, product of PIERCE) may also be used.

In the case where the labeling substance is an enzyme, a substrate for measuring the activity of the enzyme, and an optional chromogenic agent are used. Specific embodiments include the following. When peroxidase is used as an enzyme, hydrogen peroxide is used as a substrate, and o-phenylenediamine, 3,3',5,5'-tetramethylbenzidine, ammonium 2,2'-azinodi-[3-ethylbenzthiazolinesulfonate] or the like is used as a chromogenic agent. When alkaline phosphatase is used as an enzyme, p-nitrophenyl phosphate, 3-(4-methoxyspiro{1,2-dioxetane-3,2'-tricyclo-[3.3.1.1$^{3.7}$] decan}-4-yl)phenyl phosphate: AMPPD or the like is used as a substrate. When β-D-galactosidase is used as an enzyme, β-D-galactopyranoside, 4-methylumbelliferyl-β-D-galactopyranoside, or the like is used as a substrate. When glucose oxidase is used as an enzyme, β-D-glucose is used as a substrate in the co-presence of peroxidase, and a peroxidase chromogenic agent is used as a chromogenic agent.

In immunoturbidimetry (TIA or LTIA), a sample which has been treated with the amphoteric surfactant of the present invention is reacted sequentially or simultaneously with two anti-soluble LR11 antibodies (immobilized on latex particles or the like in the case of LTIA). In immunochromatography, a sample which has been treated with the amphoteric surfactant of the present invention is captured by one anti-soluble LR11 antibody immobilized on a membrane or the like, and the soluble LR11 is detected by the other anti-soluble LR11 antibody labeled with metal colloid (e.g., gold colloid) or colored latex.

Even in the case of a biological sample containing a substance interfering with immune reaction etc. (e.g., serum), when the sample is treated with the aforementioned amphoteric surfactant and subsequently subjected to an immunological assay by use of an antibody that reacts with soluble LR11, soluble LR11 present in the sample can be correctly quantitated in a simple manner. Thus, the present invention can provide a reagent for use in carrying out the immunological assay of soluble LR11, which reagent contains an anti-soluble LR11 antibody and the aforementioned specific amphoteric surfactant. Also, the anti-soluble LR11 antibody and the aforementioned specific amphoteric surfactant can be used for producing the soluble LR11 immunological assay reagent.

The immunological assay reagent contains an anti-soluble LR11 antibody and the aforementioned specific amphoteric surfactant. These ingredients may be present separately in a sample-diluting liquid and an assay reagent, or in a first reagent and a second reagent, or may be present together as a mixture. The assay reagent may further contain any ingredient for use in the detection of soluble LR11, such as a buffer, a stabilizer, or a reaction container.

Specific examples of the immunological assay reagent include the following.

In sandwich ELISA, examples include a sample-diluting liquid containing the amphoteric surfactant of the present invention, a labeled antibody liquid containing the amphoteric surfactant of the present invention, and an anti-soluble LR11 antibody-immobilized microplate containing the amphoteric surfactant of the present invention in a dry state. In LTIA, examples include a reagent liquid containing the amphoteric surfactant of the present invention but containing no anti-soluble LR11 antibody-immobilized latex particles, and a reagent liquid containing the amphoteric surfactant of the present invention and anti-soluble LR11 antibody-immobilized latex particles. In immunochromatography, examples include a sample-diluting liquid containing the amphoteric surfactant of the present invention, and a strip for immunochromatography (test strip) having the surfactant of the present invention with which a sample pad or a labeled antibody-containing pad is impregnated.

The kit for soluble LR11 immunological assay may contain an appropriate combination of the aforementioned immunological assay reagents suited for the target assay system. If required, the kit may contain other reagents required for establishing the assay system or a package insert.

EXAMPLES

The present invention will next be described in detail by way of examples, which should not be construed as limiting the invention thereto.

Example 1

Study of the Effect of the Amphoteric Surfactant of the Present Invention (Sandwich ELISA)

(1) Production of Microplate for Sandwich ELISA

An anti-soluble LR11 monoclonal antibody (M3 antibody) was diluted with 20-mmol/L phosphate buffer containing 150-mmol/L NaCl (hereinafter referred to as "PBS") (pH: 7.2) to an antibody concentration of 10 µg/mL. The thus-prepared antibody liquid was added to a 96-well microplate (product of NUNC®) at 100 µL/well. The microplate was allowed to stand for two hours at room temperature, to thereby immobilize the M3 antibody. The 96-well microplate was washed with 400 µL of PBS containing 0.05% Tween 20 (registered trademark) (hereinafter referred to as "PBST"), and 10% sucrose and 1% BSA-containing PBST (hereinafter referred to as "BSA-PBST") were added to the well at 200 µL/well. Then, the plate was blocked at room temperature for two hours. The liquid remaining in the wells was removed, and the microplate was dried overnight in a desiccator. The dried microplate was placed in an aluminum bag with a desiccant, and the sealed aluminum bag was stored in a refrigerator until it was used.

(2) Soluble LR11 Assay Through Sandwich ELISA

Each of the surfactants described below was added to PBS in such an amount that the surfactant concentration was adjusted to 5.0%, to thereby provide a sample-diluting liquid. A human serum (purchased from TENNESSEE BLOOD SERVICES INC. and having a soluble LR11 concentration, as determined through a conventional method employing MEGA-9, of 3.9 ng/mL) (hereinafter the human serum may be referred to as "test serum") was diluted with the sample-diluting liquid at a dilution factor of 11, to thereby provide an assay sample liquid (the surfactant concentration of the assay sample liquid was 10/11 times that of the sample-diluting liquid). Each assay sample liquid was added to the microplate produced in (1) above at 100 µL/well, and the microplate was allowed to stand at room temperature for 16 hours. As described above, the antigen-antibody reaction between the immobilized anti-soluble LR11 antibody and soluble LR11 present in the assay sample may be referred to as "primary reaction."

<Used Surfactants>

Comparative Example

N-acyl-N-methylglucamine

MEGA-9: Catalogue No. M015, product of Dojindo

Examples

SB10: Catalogue No. D4266, product of SIGMA-ALDRICH
SB12: Catalogue No. A1460, product of Applichem
SB14: Catalogue No. A1162, product of Applichem
CHAPS: Catalogue No. C008, product of Dojindo
CHAPSO: Catalogue No. 0020, product of Dojindo The wells of the microplate were washed thrice with PBST (400 µL×3). Separately, a biotin-labeled anti-soluble LR11 monoclonal antibody (R14 antibody, biotinylated with biotinylating agent (product of Pierce™)) was diluted with BSA-PBST to 0.4 µg/mL. The thus-diluted antibody was added to the microplate at 100 µL/well, and the plate was allowed to stand at room temperature for 4 hours. The reaction between the biotin-labeled anti-soluble LR11 monoclonal antibody (R14 antibody) and soluble LR11 captured by the microplate in the primary reaction may be referred to as "secondary reaction." The microplate was washed with PBST. Separately, peroxidase-labeled streptavidin (product of PIERCE) diluted with BSA-PBST to a concentration of 0.2 µg/mL. The thus-diluted streptavidin was added to the microplate at 100 µL/well, and the microplate was allowed to stand at room temperature for one hour. The microplate was again washed with PBST, and a TMB substrate liquid (0.3-mg/mL 3,3'-5,5'-tetramethyl-benzidine dihydrochloride (product of SIGMA), and 100-mmol/L citrate buffer containing 12-mmol/L hydrogen peroxide (pH: 3.7)) was added to the microplate at 100 µL/well. The plate was allowed to stand at room temperature for 30 minutes. Subsequently, 1.5N sulfuric acid was added to the plate at 100 µL/well, to thereby terminate color development. The absorbance of the microplate was measured at 450 nm by means of a microplate reader.

(3) Results

When any of SB10, SB12, SB14, CHAPS, and CHAPSO was used, the measured absorbance was equal to or higher than that obtained by use of MEGA-9 (FIG. 1: the absorbance in the graph is a net absorbance; i.e., (absorbance of sample)-(absorbance of blank)). As is clear from FIG. 1, the amphoteric surfactant of the present invention was found to enable assay of soluble LR11 present in a biological sample while eliminating the effects of interfering substances.

Example 2

Study on the Relationship Between the Amphoteric Surfactant (of the Present Invention) Concentration and Absorbance of Sample (1) Method Each of SB10, SB12, SB14, CHAPS, and CHAPSO was added to PBS to thereby prepare a sample-diluting liquid such that the surfactant concentration was adjusted to 0.040, 0.08%, 0.16%, 0.31%, 0.63%, 1.25%, 2.5%, or 5.0%. A test serum was 11-fold diluted with each sample-diluting liquid, to thereby provide an assay sample liquid (the surfactant concentration of the assay sample liquid was 10/11 times that of the sample-diluting liquid). Soluble LR11 present in the sample was determined through the same procedure as employed in Example 1, including primary reaction at room temperature for 16 hours.

(2) Results

In the case of SB10 (white square), a significant difference in absorbance was observed between the sample and the blank at a surfactant concentration of about 0.63%, and the absorbance reached a plateau in a concentration range of about 1.25% to 5.0%.

In the case of SB12 (white diamond), a significant difference in absorbance was observed between the sample and the blank at a surfactant concentration of about 0.16%, and the absorbance reached a peak at a surfactant concentration of about 0.63% and a plateau in a concentration range of about 0.63% to 5.0%.

In the case of SB14 (white triangle), a significant difference in absorbance was observed between the sample and the blank at a surfactant concentration of about 0.08%, and the absorbance reached a plateau in a concentration range of about 1.25% to 5.0%.

Figure 2:
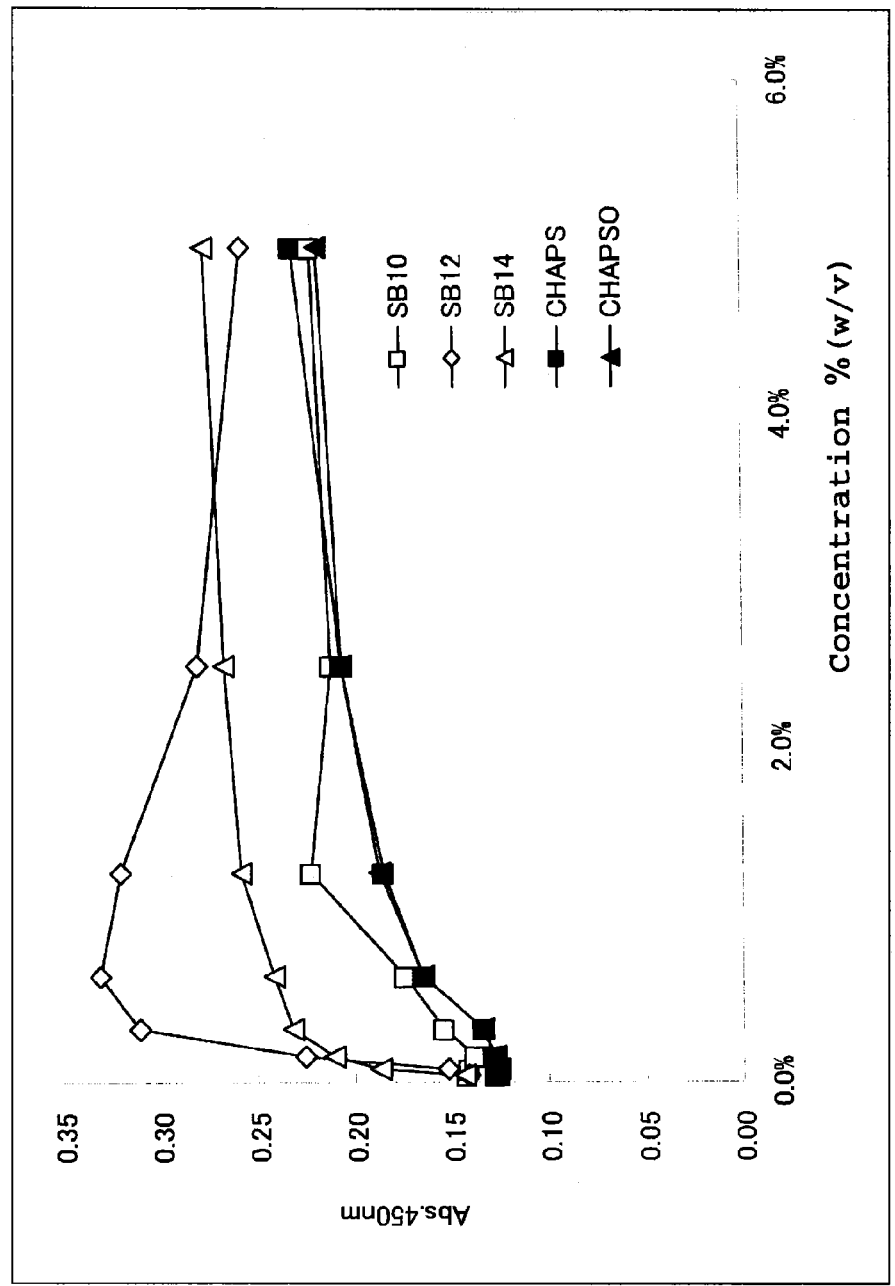
FIG. 2 A graph showing the relationship between absorbance of a sample and the concentration of the amphoteric surfactant of the present invention, when primary reaction was performed for 16 hours.

In the cases of CHAPS (black square) and CHAPSO (black triangle), significant difference in absorbance was observed between the sample and the blank at a surfactant concentration of about 0.63%, and the absorbance reached a plateau in a concentration range of about 2.5% to 5.0% (FIG. 2: the absorbance in the graph is an absorbance from which a blank value has not been subtracted).

As is clear from FIG. 2, any of the tested amphoteric surfactants of the present invention were found to enable a soluble LR11 immunological assay in a wide surfactant concentration range.

Example 3

Study of the effect of shortening reaction time by the amphoteric surfactant of the present invention (1) Method In consideration of the results of Example 2, each of SB10, SB12, SB14, CHAPS, and CHAPSO was added to PBS to thereby prepare a sample-diluting liquid such that the surfactant concentration was adjusted to 1.5%, 0.63%, 3.6%, 5.0%, and 5.0%. A test serum was 11-fold diluted with each sample-diluting liquid, to thereby provide an assay sample liquid (the surfactant concentration of the assay sample liquid was 10/11 times that of the sample-diluting liquid). Soluble LR11 present in the sample was determined through the same procedure as employed in Example 1, except that the primary reaction was performed for 1 hour, and the secondary reaction was performed for 2 hours. As Comparative Example, the same procedure was carried out by use of PBS containing MEGA-9 at 5.0% as a sample-diluting liquid.

(2) Results

Figure 3:
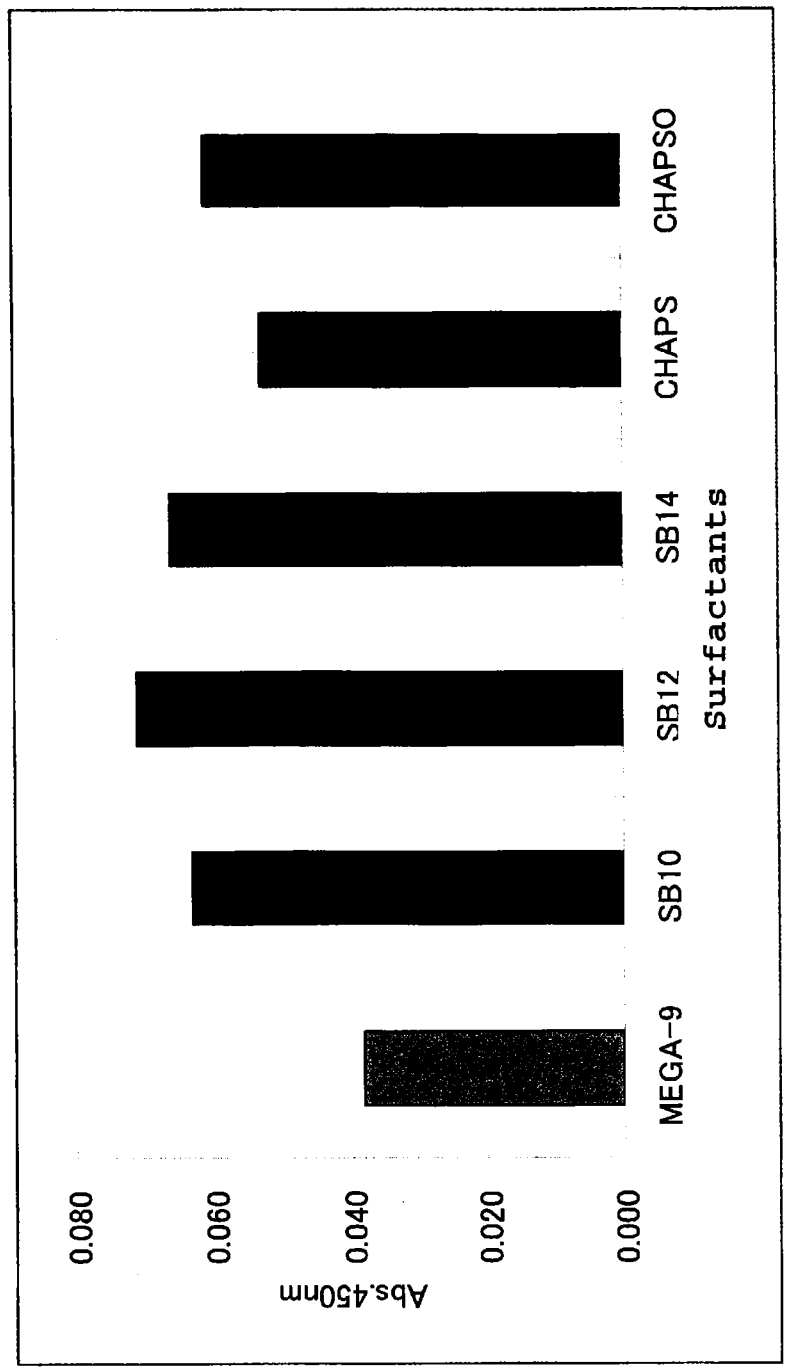
FIG. 3 A graph showing the soluble LR11 measurements obtained when primary reaction was performed for 1 hour and a surfactant disclosed in Patent Document 3 or the amphoteric surfactant of the present invention was employed.

When any of the amphoteric surfactants of the present invention was employed, the absorbance was higher than that obtained by use of MEGA-9 (Comparative Example). Thus, use of the amphoteric surfactant of the present invention was found to enable detection of soluble LR11 at higher sensitivity as compared with the conventional method employing MEGA-9, even when the primary reaction was performed at room temperature for a shortened time; i.e., one hour (FIG. 3: the absorbance in the graph is a net absorbance; i.e., (absorbance of sample)–(absorbance of blank)).

Example 4

Study of Relationship in Assay Results Between Conventional Method and the Method of the Invention—1

(1) Method

Each of SB10, SB12, and SB14 was added to PBS to thereby prepare a sample-diluting liquid such that the surfactant concentration was adjusted to 1.5%, 0.63%, and 3.6%, respectively. Five human serum samples (purchased from TENNESSEE BLOOD SERVICES INC. and having a soluble LR11 concentration, as determined through a conventional method employing MEGA-9, of 3.8 ng/mL, 3.9 ng/mL, 5.4 ng/mL, 8.0 ng/mL, and 9.8 ng/mL) were each diluted with the sample-diluting liquid at a dilution factor of 11, to thereby provide assay sample liquids (the surfactant concentration of each assay sample liquid was 10/11 times that of the sample-diluting liquid). Soluble LR11 present in the sample was determined through the same procedure as employed in Example 1, except that the primary reaction was performed for 1 hour, and the secondary reaction was performed for 2 hours.

As Comparative Example, the same procedure was carried out by use of PBS containing MEGA-9 at 5.0% as a sample-diluting liquid.

The correlation in LR11 measurements between the method of the invention and the conventional method was confirmed from the results of Example 4, Comparative Example, and LR11 concentrations obtained by use of MEGA-9 (5.0%) with primary reaction for 16 hours and secondary reaction for 4 hours.

(2) Results

Figure 4:
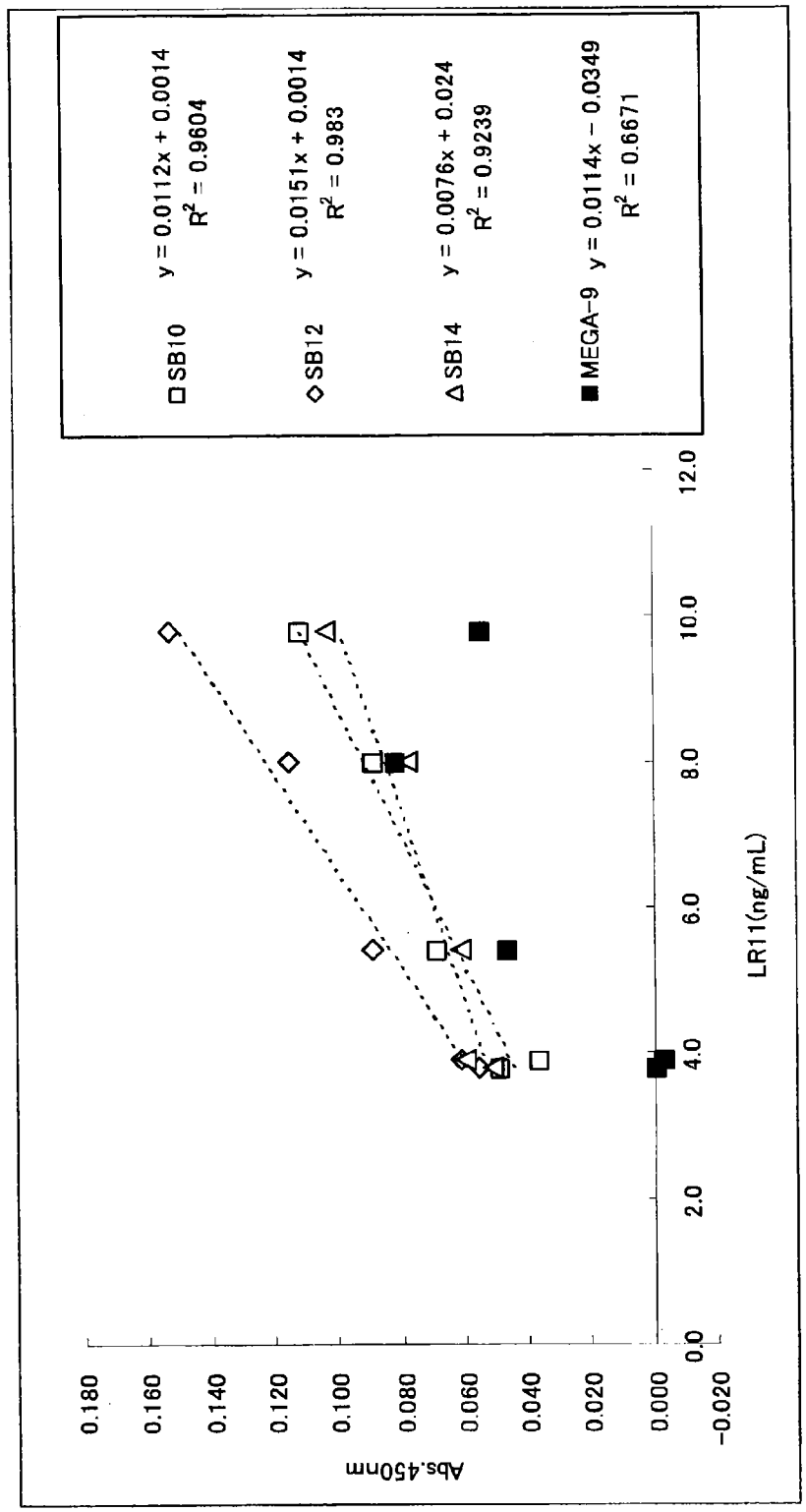
FIG. 4 A graph showing the correlation between the soluble LR11 measurements obtained when primary reaction was performed for 1 hour and a surfactant disclosed in Patent Document 3 or the amphoteric surfactant of the present invention (vertical axis) was employed, and the soluble LR11 measurements obtained by the conventional assay method when primary reaction was performed for 16 hours and a surfactant disclosed in Patent Document 3 (horizontal axis) was employed.

FIG. 4 shows the correlation of the soluble LR11 measurements (vertical axis) when primary reaction and secondary reaction were performed for 1 hour and 2 hours, respectively, and the amphoteric surfactant of the present invention or MEGA-9 (Comparative Example) was used, with the results of the conventional assay method (horizontal axis) when primary reaction and secondary reaction were performed for 16 hours and 4 hours, respectively, and MEGA-9 was used. In FIG. 4, the absorbance in the graph is a net absorbance; i.e., (absorbance of sample)–(absorbance of blank).

In Comparative Example (5.0% MEGA-9, primary reaction: 1 hour, and secondary reaction: 2 hours) (black square), the absorbance of the sample of 9.8 ng/mL was merely slightly higher than that of the sample of 5.4 ng/mL. The absorbance of the sample of 8.0 ng/mL was higher than that of the sample of 9.8 ng/mL. The absorbance values of the samples of 3.8 and 3.9 ng/mL were considerably lower than the absorbance of the sample of 5.4 ng/mL.

In contrast, in the case where soluble LR11 was determined by use of the amphoteric surfactant of the present invention (primary reaction: 1 hour and secondary reaction: 2 hours), in any case of use the amphoteric surfactants (SB10 (white diamond), SB12 (white square), and SB14 (white triangle)), the absorbance measurements of each serum sample were found to be in the same relationship as that of the absorbance measurements obtained through the conventional method, indicating the existence of concentration-dependence of absorbance (FIG. 4).

Example 5

Study of Relationship in Assay Results Between Conventional Method and the Method of the Invention—2

(1) Method

Each of CHAPS and CHAPSO was added to PBS to thereby prepare a sample-diluting liquid such that the surfactant concentration was adjusted to 5.0%. Six human serum samples (purchased from TENNESSEE BLOOD SERVICES INC. and having a soluble LR11 concentration, as determined through a conventional method employing MEGA-9, of 3.1 ng/mL, 5.2 ng/mL, 6.7 ng/mL, 7.2 ng/mL, 8.7 ng/mL, and 9.5 ng/mL) were each diluted with the sample-diluting liquid at a dilution factor of 11, to thereby provide assay sample liquids (the surfactant concentration of each assay sample liquid was 10/11 times that of the sample-diluting liquid). Soluble LR11 present in the sample was determined through the same procedure as employed in Example 1, except that the primary reaction was performed for 1 hour, and the secondary reaction was performed for 2 hours.

The correlation in LR11 measurements between the method of the invention and the conventional method was confirmed from the results of Example 5 and LR11 concentrations obtained by use of PBS containing MEGA-9 (5.0%) serving as a sample-diluting liquid with primary reaction for 16 hours and secondary reaction for 4 hours (Comparative Example).

(2) Results

Figure 5:
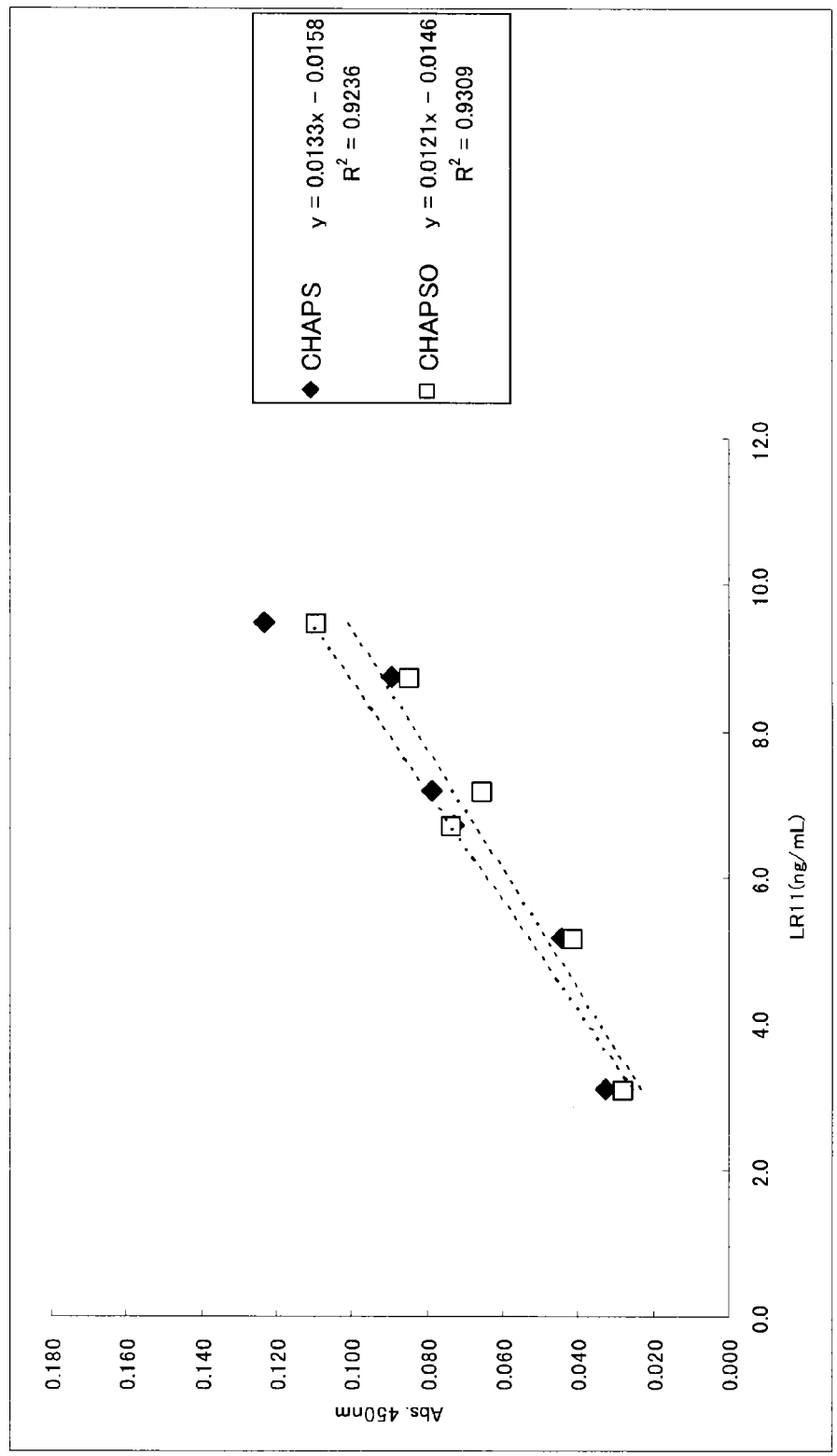
FIG. 5 A graph showing the correlation between the soluble LR11 measurements obtained when primary reaction was performed for 1 hour and a surfactant disclosed in Patent Document 3 or the amphoteric surfactant of the present invention (vertical axis) was employed, and the soluble LR11 measurements obtained by the conventional assay method when primary reaction was performed for 16 hours and a surfactant disclosed in Patent Document 3 (horizontal axis) was employed.

FIG. 5 shows the correlation of the soluble LR11 measurements (vertical axis) when primary reaction and secondary reaction were performed for 1 hour and 2 hours, respectively, and the amphoteric surfactant of the present invention or MEGA-9 (Comparative Example) was used, with the results of the conventional assay method (horizontal axis) when primary reaction and secondary reaction were performed for 16 hours and 4 hours, respectively, and MEGA-9 was used. In FIG. 5, the absorbance in the graph is a net absorbance; i.e., (absorbance of sample)−(absorbance of blank).

In contrast, in the case where soluble LR11 was determined by use of the amphoteric surfactant of the present invention (primary reaction: 1 hour and secondary reaction: 2 hours), in any case of use the amphoteric surfactants (CHAPS (black diamond) and CHAPSO (white square)), the absorbance measurements of each serum sample were found to be in the same relationship as that of the absorbance measurements obtained through the conventional method, indicating the existence of concentration-dependence of absorbance (FIG. 5).

The results of Examples 4 and 5 have proven the following. Specifically, when a sample which has been treated with the amphoteric surfactant of the present invention is subjected to an immunological assay, soluble LR11 level-dependent measurement results can be obtained without affecting the concentration-absorbance relationship obtained through the conventional method. In addition, the effects of interfering substances present in the sample can be eliminated, similar to the case of N-acyl-N-methylglucamine or the like disclosed in Patent Document 3. Also, even when the primary reaction time is shortened to one hour at room temperature, soluble LR11 level-dependent measurement results can be obtained.

The invention claimed is:

1. A method for immunologically assaying soluble LR11 present in a biological sample selected from the group consisting of plasma, serum, cerebrospinal fluid and urine, the method comprising:
    treating the sample with at least one surfactant selected from the group consisting of N-decyl-N,N-dimethyl-3-ammonio-1-propanesulfonate (SB10), N-dodecyl-N,N-dimethyl-3-ammonio-1-propanesulfonate (SB12), N-tetradecyl-N,N-dimethyl-3-ammonio-1-propanesulfonate (SB14), 3-[(3-cholamidopropyl)dimethylammonio]-1-propanesulfonate (CHAPS) and 3-([3-Cholamidopropyl]dimethylammonio)-2-hydroxy-1-propanesulfonate (CHAPSO);
    reacting the treated sample with an anti-soluble LR11 antibody; and
    subjecting the reacted sample to an immunological assay.

2. The method according to claim 1, further comprising forming an immune complex from at least two antibodies having different antigen-recognition sites, wherein the at least two antibodies are anti-soluble LR11 antibodies.

3. The method according to claim 1, wherein the at least one surfactant is selected from the group consisting of SB10, SB12 and SB14.

* * * * *